United States Patent [19]
Yoon

[11] Patent Number: 5,922,001
[45] Date of Patent: *Jul. 13, 1999

[54] SURGICAL INSTRUMENT WITH JAWS AND A MOVABLE INTERNAL BLADE MEMBER AND METHOD FOR USE THEREOF

[76] Inventor: InBae Yoon, 2101 Highland Ridge Dr., Phoenix, Md. 21131

[*] Notice: This patent is subject to a terminal disclaimer.

[21] Appl. No.: 08/847,184

[22] Filed: May 1, 1997

Related U.S. Application Data

[63] Continuation-in-part of application No. 08/376,186, Jan. 20, 1995, Pat. No. 5,665,100, which is a continuation-in-part of application No. 08/281,814, Jul. 28, 1994, abandoned, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.⁶ .................................................... A61B 17/32
[52] U.S. Cl. ........................ 606/170; 606/205; 606/139; 606/144
[58] Field of Search ..................................... 606/205, 207, 606/151, 170, 142, 144, 139, 149, 148, 167

[56] References Cited

U.S. PATENT DOCUMENTS

| | | |
|---|---|---|
| 2,002,594 | 5/1935 | Wappler et al. . |
| 2,004,559 | 6/1935 | Wappler et al. . |
| 2,028,635 | 1/1936 | Wappler . |
| 4,077,412 | 3/1978 | Moossun . |
| 4,103,680 | 8/1978 | Yoon . |
| 4,174,715 | 11/1979 | Hasson . |
| 4,249,533 | 2/1981 | Komiya . |
| 4,257,420 | 3/1981 | Terayama . |
| 4,372,295 | 2/1983 | Heckele . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,557,255 | 12/1985 | Goodman . |
| 4,598,699 | 7/1986 | Garren et al. . |
| 4,788,966 | 12/1988 | Yoon . |
| 4,869,268 | 9/1989 | Yoon . |
| 4,966,583 | 10/1990 | Debbas . |
| 5,025,778 | 6/1991 | Silverstein et al. . |
| 5,037,433 | 8/1991 | Wilk et al. . |
| 5,139,487 | 8/1992 | Baber . |
| 5,147,373 | 9/1992 | Ferzli . |
| 5,176,695 | 1/1993 | Dulebohn . |
| 5,190,541 | 3/1993 | Abele et al. . |
| 5,211,650 | 5/1993 | Noda . |
| 5,217,460 | 6/1993 | Knoepfler . |
| 5,226,908 | 7/1993 | Yoon . |
| 5,234,443 | 8/1993 | Phan et al. . |
| 5,261,917 | 11/1993 | Hasson et al. . |
| 5,312,391 | 5/1994 | Wilk . |

(List continued on next page.)

*Primary Examiner*—Michael Buiz
*Assistant Examiner*—Daphna Shai
*Attorney, Agent, or Firm*—Blank Rome Comisky & McCauley LLP

[57] ABSTRACT

An endoscopic instrument includes a forceps unit for being positioned within an anatomical cavity and inner member having a blade. The forceps unit includes a housing, an outer tubular member, an intermediate member, and a handle mechanism coupled with at least one of the intermediate and outer tubular members for creating relative movement between the intermediate and outer tubular members. The outer tubular member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The inner member includes a tubular member removably disposed at least partly within the intermediate member and a blade for performing surgical functions.

21 Claims, 9 Drawing Sheets

U.S. PATENT DOCUMENTS

| | | |
|---|---|---|
| 5,318,589 | 6/1994 | Lichtman . |
| 5,324,254 | 6/1994 | Phillips . |
| 5,336,231 | 8/1994 | Adair . |
| 5,348,555 | 9/1994 | Zinnanti . |
| 5,366,476 | 11/1994 | Noda . |
| 5,398,670 | 3/1995 | Ortiz et al. . |
| 5,403,332 | 4/1995 | Christoudias . |
| 5,462,561 | 10/1995 | Voda . |
| 5,462,562 | 10/1995 | Elkus . |
| 5,476,505 | 12/1995 | Limon . |
| 5,496,310 | 3/1996 | Exconde et al. . |
| 5,538,008 | 7/1996 | Crowe . |
| 5,542,949 | 8/1996 | Yoon . |
| 5,549,623 | 8/1996 | Sharpe et al. . |
| 5,562,102 | 10/1996 | Taylor . |
| 5,569,241 | 10/1996 | Edwards . |
| 5,578,007 | 11/1996 | Imran . |
| 5,607,435 | 3/1997 | Sachdeva et al. . |
| 5,611,813 | 3/1997 | Lichtman . |
| 5,620,459 | 4/1997 | Lichtman . |
| 5,746,770 | 5/1998 | Zeitels et al. . |
| 5,766,169 | 6/1998 | Fritzsch et al. . |

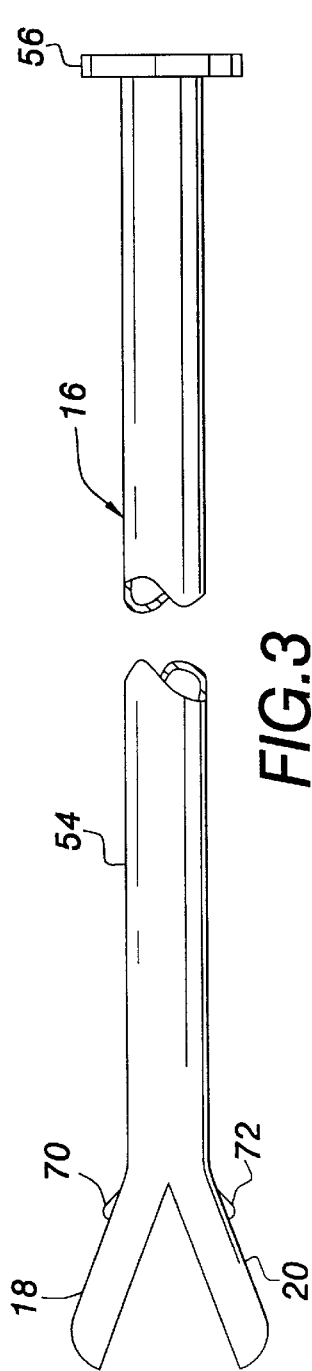
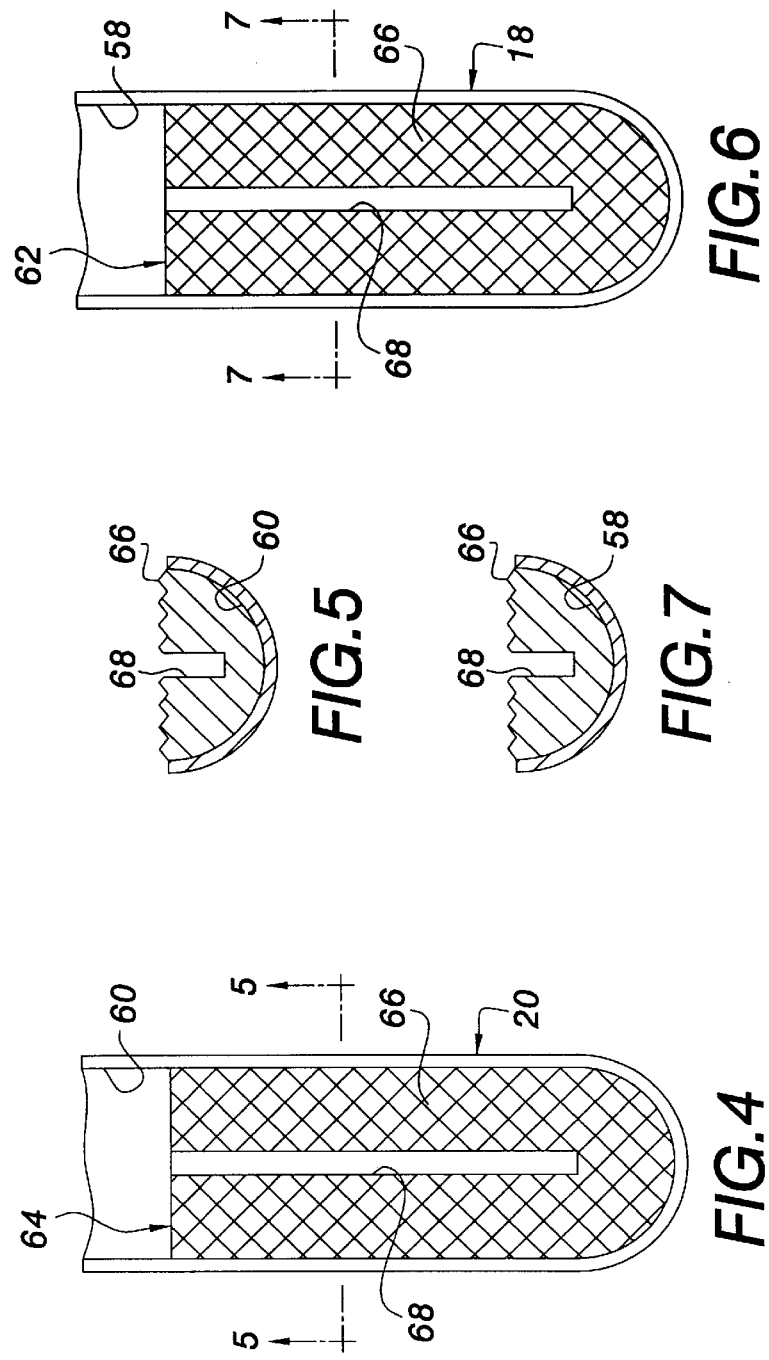

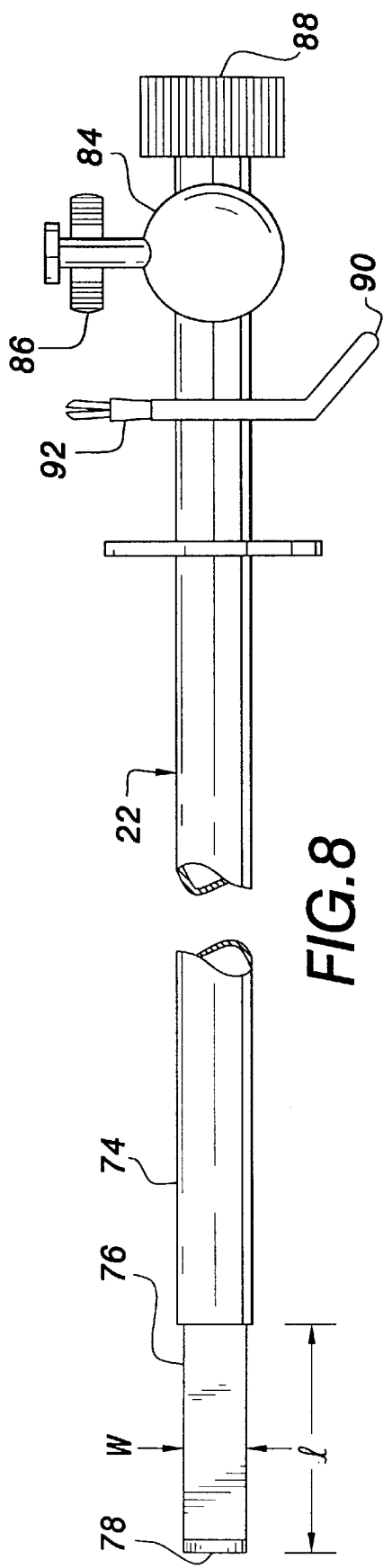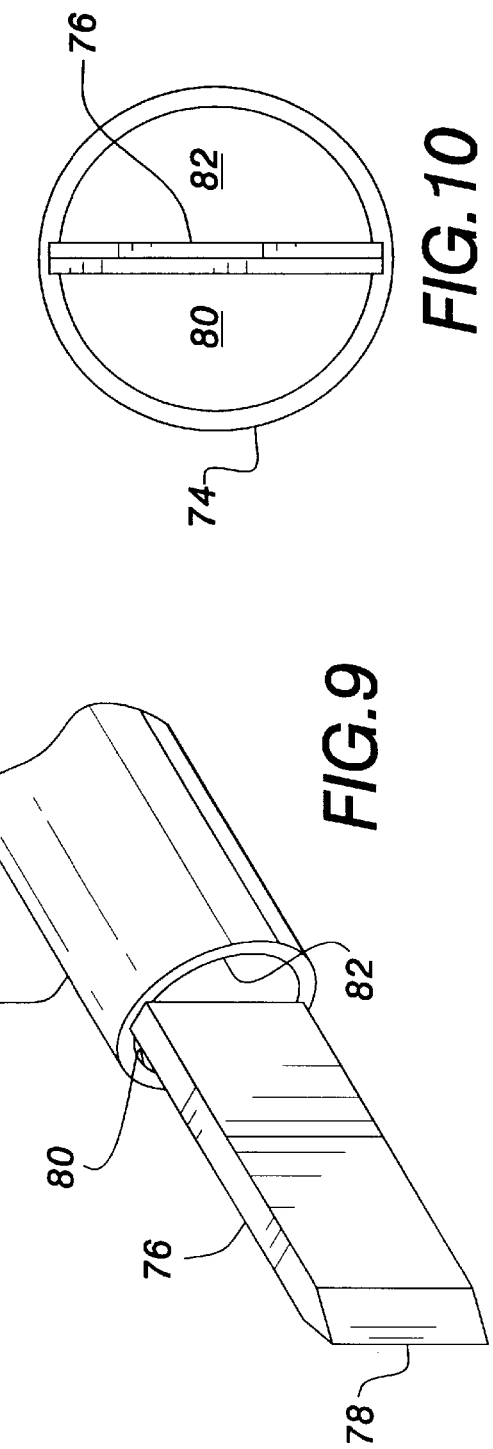
FIG. 8
FIG. 9
FIG. 10

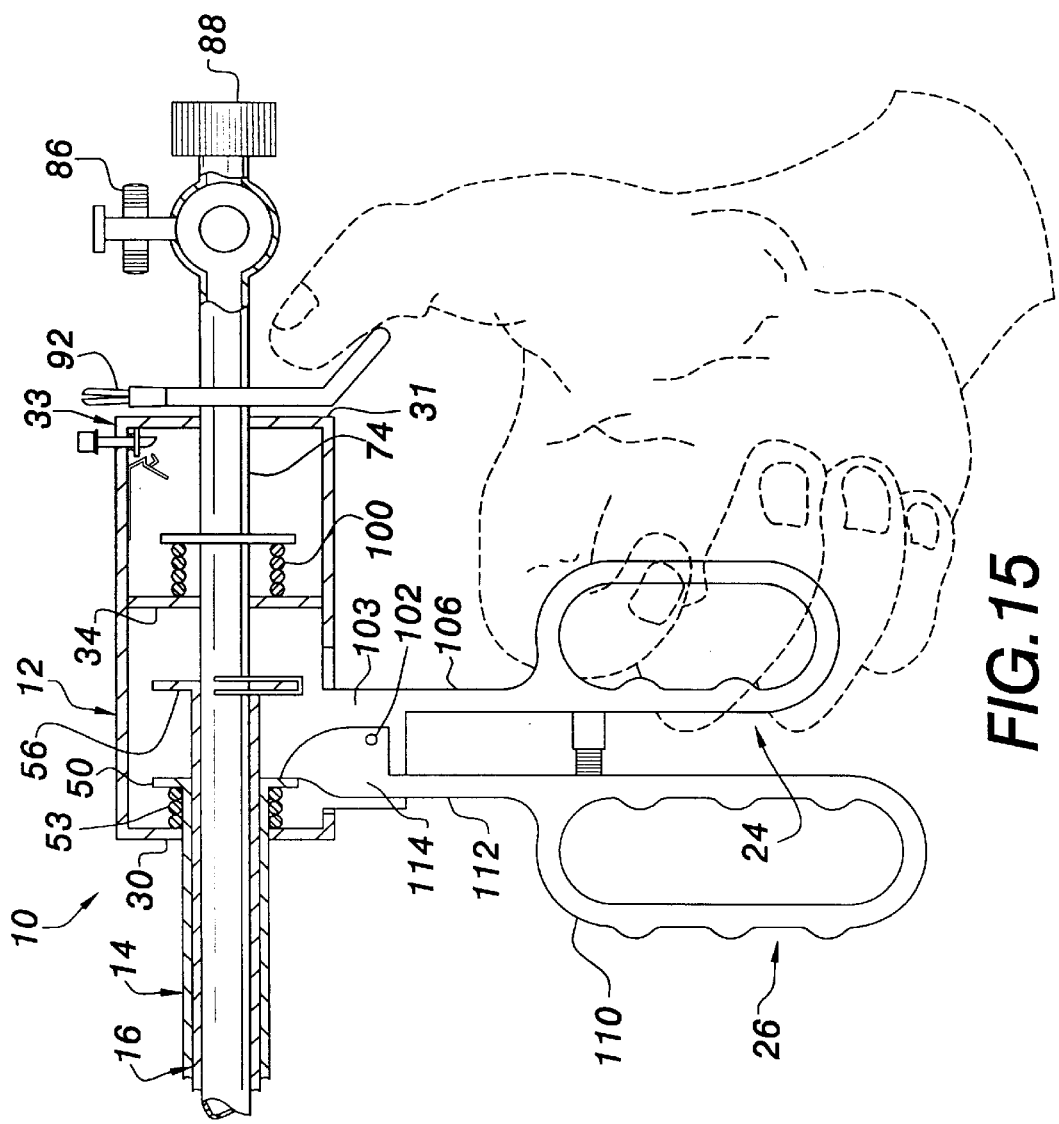
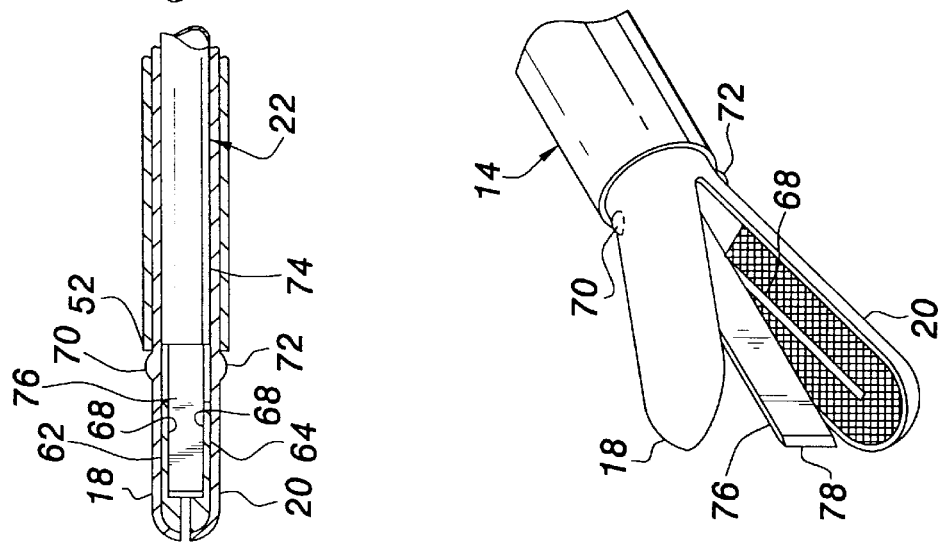
FIG.15
FIG.16

SURGICAL INSTRUMENT WITH JAWS AND A MOVABLE INTERNAL BLADE MEMBER AND METHOD FOR USE THEREOF

CROSS-REFERENCE TO RELATED APPLICATIONS

This application is a continuation-in-part of applicant's patent application Ser. No. 08/376,186, filed on Jan. 20, 1995, now U.S. Pat. No. 5,665,100, which is a continuation-in-part of patent application Ser. No. 08/281,814, filed Jul. 28, 1994, abandoned which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to medical procedures and instruments and, more particularly, to a multi-functional instrument having jaws, a central channel formed therethrough and a moveable blade member disposed in the central channel for performing endoscopic surgical procedures.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

SUMMARY OF THE INVENTION

Accordingly, it is a primary object of the present invention to overcome the above mentioned disadvantages of the prior art with an endoscopic instrument capable of performing multiple functions.

Another object of the present invention is to minimize the number of incisions required for performing an endoscopic procedure by performing multiple functions through a single incision with an endoscopic instrument having a forceps unit with jaws for performing grasping functions and a movable blade member in the jaws for performing the function of cutting, manipulating or cauterizing.

It is another object of the present invention to hold jaws of an endoscopic instrument together to ensure smooth entry of the endoscopic instrument through a portal sleeve and to prevent inadvertent snagging of anatomical tissue.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and a blade member is facilitated, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity, a channel formed through the forceps unit, and a moveable inner member having a blade disposed in the channel. The forceps unit includes a housing, a tubular outer member, an intermediate member, and a handle mechanism coupled with at least one of the intermediate and outer members for creating relative movement therebetween. The outer member has a proximal end mounted in the housing and terminates distally at a distal end. The intermediate member has a tubular body disposed telescopically within the outer member, a proximal end mounted in the housing and an integral one-piece distal end defining a pair of opposed jaws resiliently biased apart such that relative movement of the outer member distal end over the jaws causes the jaws to close. The movable inner member includes an inner shaft disposed at least partly within the intermediate member and having a blade on a distal end for performing at least one of the functions of cutting, cauterizing, manipulating, and dissecting.

Another aspect of the present invention is generally characterized in a method of performing an endoscopic procedure including the steps of introducing a tubular member with integral one-piece jaws through an opening in an anatomical cavity wall, grasping anatomical tissue with the jaws, advancing a moveable inner member having a blade distally through the tubular member, and performing a medical procedure involving at least one of the functions of cutting, dissecting, and cauterizing the blade member.

Yet another aspect of the present invention is generally characterized in a method of performing endoscopic procedures including the steps of introducing a tubular member with integrally formed jaws through an opening in an anatomical cavity wall, advancing an inner member having a blade distally through the tubular member until the blade protrudes distally from the jaws and performing a medical procedure with the blade.

An additional aspect of the present invention is generally characterized in a method of performing endoscopic procedures including the steps of introducing a tubular member with integrally formed jaws through an opening in an anatomical cavity wall, advancing an inner member having a blade distally through the tubular member until the blade is disposed between the jaws, opening the jaws to permit the blade to be exposed, positioning anatomical tissue proximate the blade, and cutting tissue with the blade while the jaws are either opened of closed.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 illustrates the intermediate member of the preferred embodiment removed from the outer member for illustrative purposes;

FIG. 4 illustrates one jaw of the preferred embodiment;

FIG. 5 illustrates the jaw of FIG. 4 in section taken along line 5—5;

FIG. 6 illustrates the other jaw of the preferred embodiment;

FIG. 7 illustrates the jaw of FIG. 5 in section taken along line 7—7;

FIG. 8 illustrates the inner member of the preferred embodiment removed from the outer member and the intermediate member for illustrative purposes;

FIG. 9 is a perspective view of the distal end of the inner member;

FIG. 10 illustrates the inner member as viewed from the distal end;

FIG. 15 is a sectional view of the preferred embodiment with the jaws closed and the inner member advanced distally;

FIG. 16 illustrates the distal end of the preferred embodiment with the jaws open and the inner member advanced;

FIGS. 18—21 illustrate modifications of the jaws of the preferred embodiment; and FIG. 22 illustrates the distal end of a modified outer member.

DETAILED DESCRIPTION OF THE PREFERRED EMBODIMENT

The endoscopic instrument of the present invention can be utilized in any type of anatomical cavity. Accordingly, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
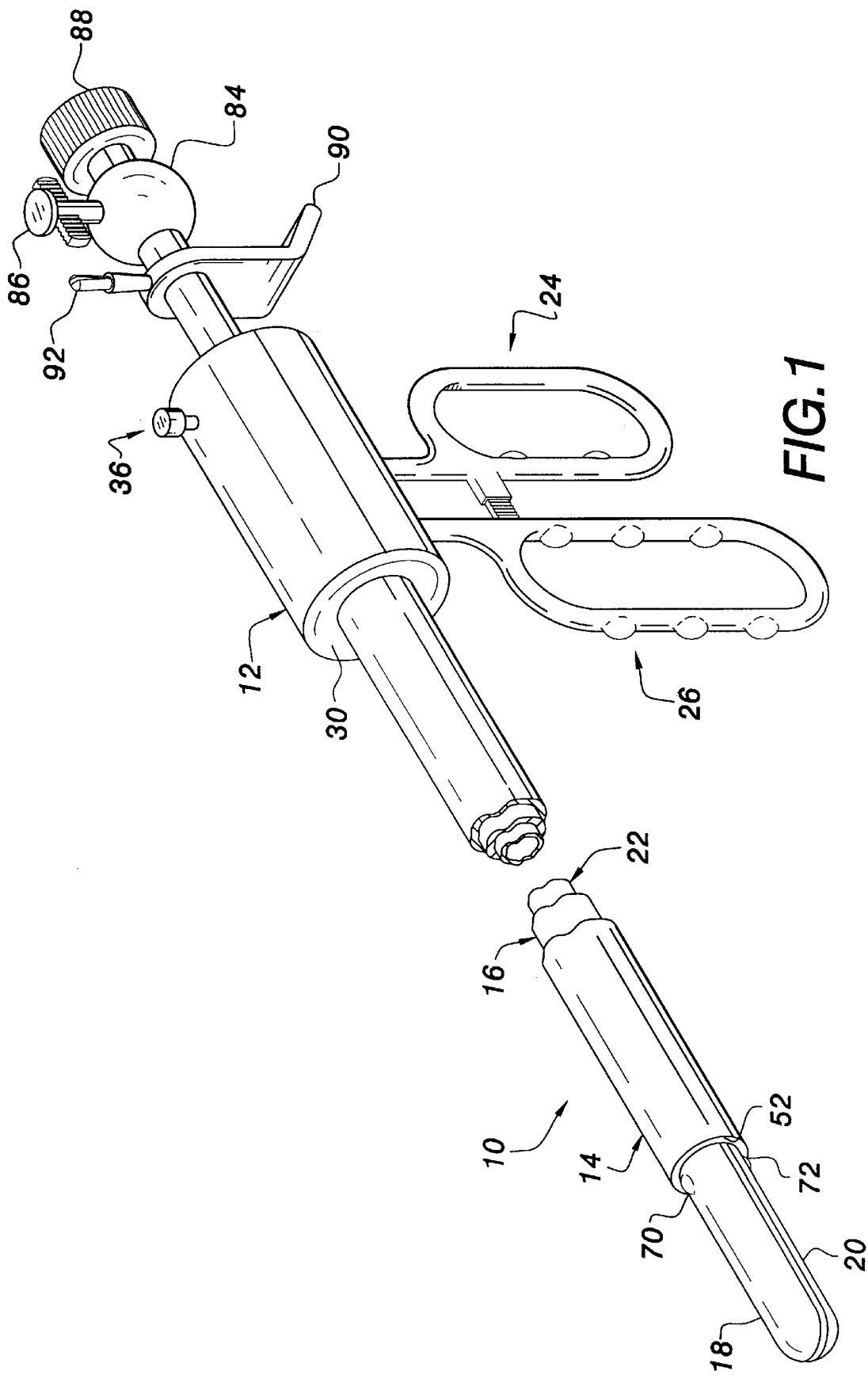
FIG. 1 is a perspective view, broken longitudinally, of an endoscopic instrument according to a preferred embodiment the present invention.
Figure 2:
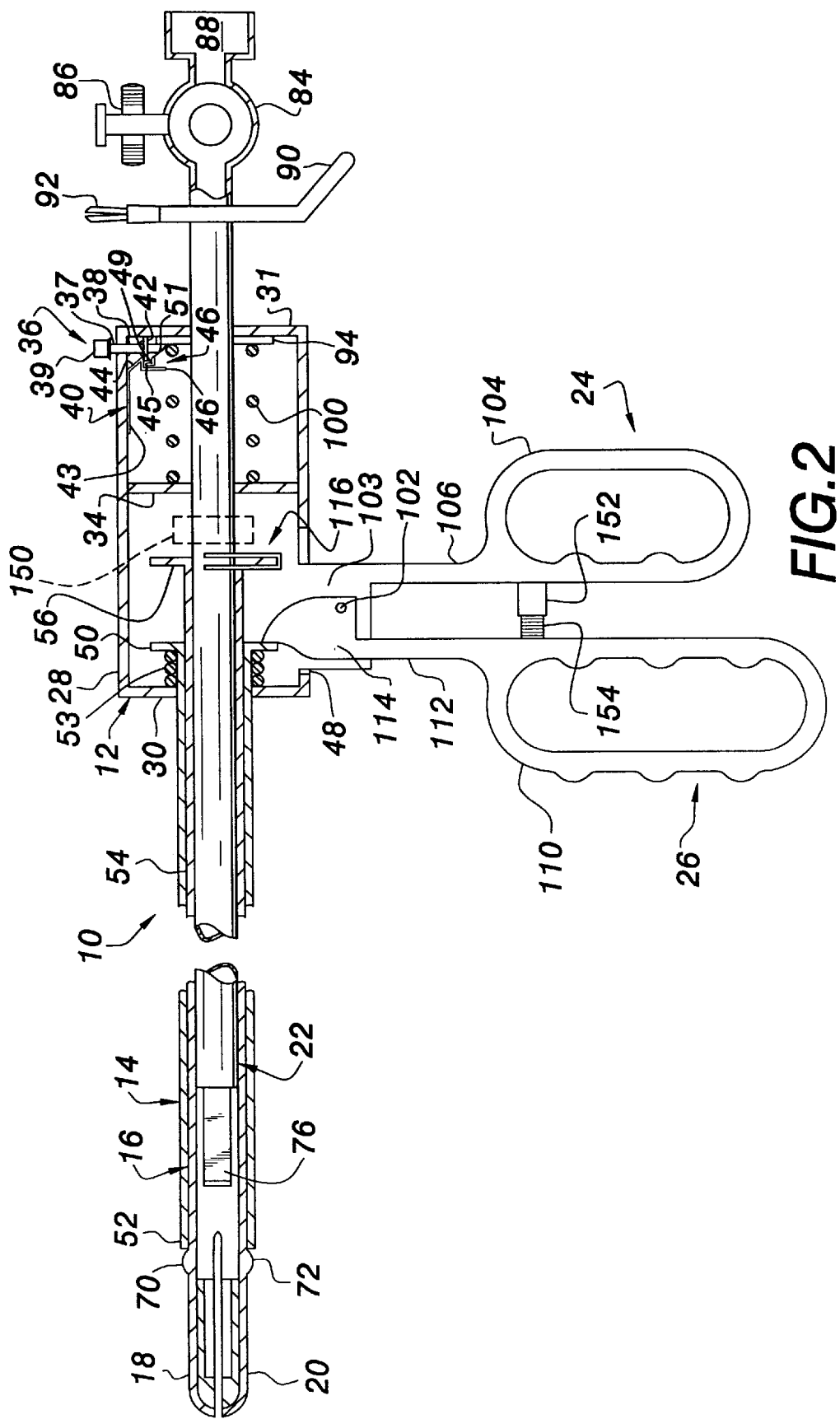
FIG. 2 is a sectional view of the preferred embodiment.

An endoscopic instrument 10 according to a preferred embodiment of the present invention, as shown in FIGS. 1 and 2, includes housing 12, tubular outer member 14 extending distally from the housing 12, tubular intermediate member 16 telescopically fitted within outer member 14 and having opposed jaws 18 and 20 on a distal end thereof, a fixed handle 24 and a movable handle 26. Inner member 22 is at least partly telescopically fitted within intermediate member 16.

Housing 12 is generally tubular with cylindrical sidewall 28 and front and rear walls 30 and 31 closing opposite ends of the cylindrical sidewall 28. Intermediate wall 34 divides housing 12 into two compartments. Slotted opening 48 is formed in the cylindrical sidewall 28 of housing 12 and extends longitudinally between front wall 30 and intermediate wall 34 of housing 12 to permit movable handle 26 to pass therethrough. Fixed handle 24 extends from plate 103 formed on housing 12 proximate slot 48. Plate 103 can be formed integrally with housing 12 or can be fixedly attached to housing 12 to be stationary relative thereto.

Outer member 14 is open at both ends and extends through an opening in front wall 30 to terminate proximally at transverse flange 50 disposed between front wall 30 and intermediate wall 34 of housing 12. Distal end 52 of outer member 14 can be blunt as shown, tapered, beveled or chamfered as desired or have any other suitable distal configuration. Preferably, outer member 14 is made of a substantially cylindrical length of a substantially rigid material, such as stainless steel or other medically acceptable plastic or metal material.

Intermediate member 16 includes tubular body 54 telescopically fitted within the outer tubular member 14. Tubular body 54 terminates proximally at transverse flange 56 disposed within housing 12 between outer tubular member flange 50 and intermediate wall 34 and, as best seen in FIGS. 3–7 which show intermediate member 16 removed from outer member 14 for illustrative purposes, a distal end of tubular body 54 is split longitudinally to form integral one-piece jaws 18 and 20 that oppose one another. Jaws 18 and 20 are normally biased apart as shown and define opposed semicylindrical recesses 58 and 60 (see FIGS. 5 and 7) for carrying jaw inserts 62 and 64.

Jaw inserts 62 and 64 can be permanently or removably secured within semicylindrical recesses 58 and 60 respectively using adhesives, detents, or any other suitable method of attachment or can be formed with jaws 18 and 20 respectively as an integral one-piece construction. Each insert defines a grasping surface or tread 66 suitable for grasping anatomical tissue or holding instruments, such as a needle, and a longitudinal slot or groove 68 extending from a proximal end of the insert to a position proximally spaced from the distal end of the insert. A repeated pattern of diamond-shaped protrusions is shown for tread 66. However, other surfaces such as those having parallel ribs or textured portions could be used. The depth of each groove 68 will depend on the size of a blade member disposed on a distal end of inner member 22 as will be described in more detail below. Wedge-like cams 70 and 72 are formed on respective exterior surfaces of jaws 18 and 20 and are distally spaced from outer member distal end 52 when jaws 18 and 20 are entirely open (see FIG. 12). Cams 70 and 72 taper toward the joint region or junction where each jaw connects with tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing the upper and lower jaws 18 and 20 apart while permitting jaws 18 and 20 to be moved towards one another in response to axial forces as a result of relative movement between outer member 14 and intermediate member 16. Referring again to FIG. 2, it can be seen that bias member 53 is connected between outer member flange 50 and front wall 30 such that outer member 14 is normally biased in a proximal direction relative to intermediate member 16. Bias member 53 is shown as a helical coil spring disposed around intermediate member 16 and held in compression between outer member flange 50 and front wall 30. However, bias member 53 can be constituted of various other types of springs as well as other types of bias devices including tension springs, torsion springs, pan springs, leaf springs, rubber, plastic or magnets, for example. Flange 56 of intermediate member 16 is fixed to housing 12 by bracket 116.

As best seen in FIGS. 8–10, which illustrate inner member 22 removed from outer member 14 and intermediate member 16 for illustrative purposes, inner member 22 includes a cylindrical or tubular shaft 74 and flat single-edge cutting blade 76 mounted at a distal end of tubular shaft 74. Blade 76 has a width w that is slightly less than the diameter of the tubular shaft 74, a length 1 that is approximately equal to or greater than the length of slots 68 in jaw inserts 62 and 64, and a thickness that is suitable for sliding within slots 68. Blade 76 of this preferred embodiment has straight cutting edge 78 oriented substantially perpendicularly relative to the longitudinal axis of the instrument. However, slanted, curved, serrated or toothed cutting edges could also be used. Blade 76 extends diametrically across the open distal end of tubular shaft 74 leaving openings 80 and 82 on either side of blade 76 for communicating with the passage formed by tubular shaft 74 (See FIGS. 9 and 10). Referring to FIG. 2, tubular shaft 74 is telescopically fitted within the tubular portion of intermediate member 16 and extends through aligned openings in front and rear walls 30 and 31 and intermediate wall 34 of housing 12 to terminate proximally outside housing 12 at spherical reservoir 84 with a proximal aperture 88 and stop cock valve 86 disposed within reservoir 84 for controlling passage of instruments and/or fluids through aperture 88 and into tubular shaft 74.

Handle 90 extends transversely from tubular shaft 74 near the proximal end of tubular shaft 74 and is angled proximally to form a finger rest. An insulated connector 92 can be provided to permit electrical conductors to enter the tubular shaft 74 on a side opposite handle 90 to be connected with electrically conductive elements of the instrument for performing unipolar or bipolar electric coagulation, for example using the blade 76 or jaws 18 and 20 as a conductive element. Tubular shaft 74 also carries transverse flange 94 disposed within housing 12 between rear wall 31 and intermediate wall 34 (see FIG. 2). Bias member 100, shown as a helical coil spring, is disposed around tubular shaft 74 and held in compression between flange 94 and intermediate wall 34 to bias inner member 22 proximally within housing 12 and intermediate member 16.

Inner member 22 is prevented from being inadvertently moved in a distal direction by a safety mechanism 36 disposed within the housing 12 as shown in FIG. 2. A push-button type of safety mechanism 36, as disclosed in the parent application, is shown whereby inner tubular member 22 can be locked in a retracted position with flange 94 abutting rear wall 31 by depressing button 39 and can subsequently be released prior to being moved distally by depressing button 39 a second time. It will be appreciated, however, that other safety mechanisms can be used, including rotatable levers, detents, and splined collars for example. Safety mechanism 36 includes post 37 extending radially through housing 12, bias member 38 connected between post 37 and housing 12 for biasing post 37 radially outward, push-button 39 mounted on top of post 37 externally of housing 12 latch spring 40 disposed within housing 12 for engaging post 37 in a locked position where a lower end of post 37 engages flange 94, and trigger 41 for releasing latch spring 40 to allow post 37 to move radially outward to an unlocked position. Post 37 is oriented transversely relative to the longitudinal axis of inner member 22 and includes annular flange 42 disposed within housing 12. Bias member 38 is shown as a helical coil spring disposed around post 37 and held in tension between housing 12 and annular flange 42 to bias post 37 radially outward of housing 12. Latch spring 40 is formed of a resilient strip of material configured to have flat base 43 secured to an outer wall of the hub and downwardly angled arm 44 extending from a proximal end of base 43 toward the post 37. Arm 44 bends back on itself to form latching surface 45 that is substantially parallel annular flange 42. Transverse extension 46 of arm 44 extends from a distal end of latching surface 45 in parallel to the post 37. Trigger 41 is disposed proximate arm extension 46 and is pivotally mounted in housing 12. Trigger 41 is generally L-shaped and has leg 49 overlying arm extension 46 and leg 51 extending transversly from leg 49 and at a slight downward angle, as shown in FIG. 2, to be disposed beneath annular flange 42 when post 37 is in the locked position shown in FIG. 2. A torsion spring (not shown) can be connected between trigger 41 and housing 12 to bias trigger 41 in a counterclockwise direction in FIG. 2 such that leg 49 is normally in contact with the arm extension 46.

Referring still to FIG. 2, it will be seen that movable handle 26 is pivotally mounted on pin 102 secured to mounting plate 103 which extends outward from side wall 28 along an edge of slotted opening 48. Fixed handle 24 includes a finger loop 104 configured to accommodate one or more fingers, or the thumb, of the user and a shank 106 fixedly connected to mounting plate 103. Movable handle 26 includes a finger loop 110 configured to accommodate one or more fingers of the user and a shank 112 connecting the finger loop with a flattened end portion 114 which extends into housing 12 towards flange 50 of outer member 14 through slotted opening 48. Therefore, when movable handle 26 is pressed towards fixed handle 24, end portion 114 presses flange 50 distally. This causes distal end 52 of outer member 16 to move at least partially over cams 70 and 72 to press jaws 18 and 20 towards one another to the closed position illustrated in FIG. 2.

A pair of mating protrusions 152 and 154 are carried at opposed locations on finger loops 104 and 110 to lock handles 24 and 26 together when pressed towards one another a predetermined angular distance corresponding to a desired resultant position of jaws 18 and 20. Mating protrusions 152 and 154 are shown having serrated inside surfaces, but can have any other configuration to ratchet, mate frictionally and/or latch together when engaged.

Use of the endoscopic instrument 10 of the present invention is illustrated in FIGS. 11–17, wherein instrument 10 is shown being guided through portal sleeve 156 positioned in a wall W of an anatomical cavity. Instrument 10 is preferably passed through portal sleeve 156 with jaws 18 and 20 at least partly closed so that instrument 10 can be inserted without catching on anatomical tissue or snagging structure within portal sleeve 156. Since outer member 14 can be held by protrusions 152 and 154 in a position partly or entirely closing jaws 18 and 20, the surgeon need not exert any force on the handles of the instrument during insertion.

Figure 11:
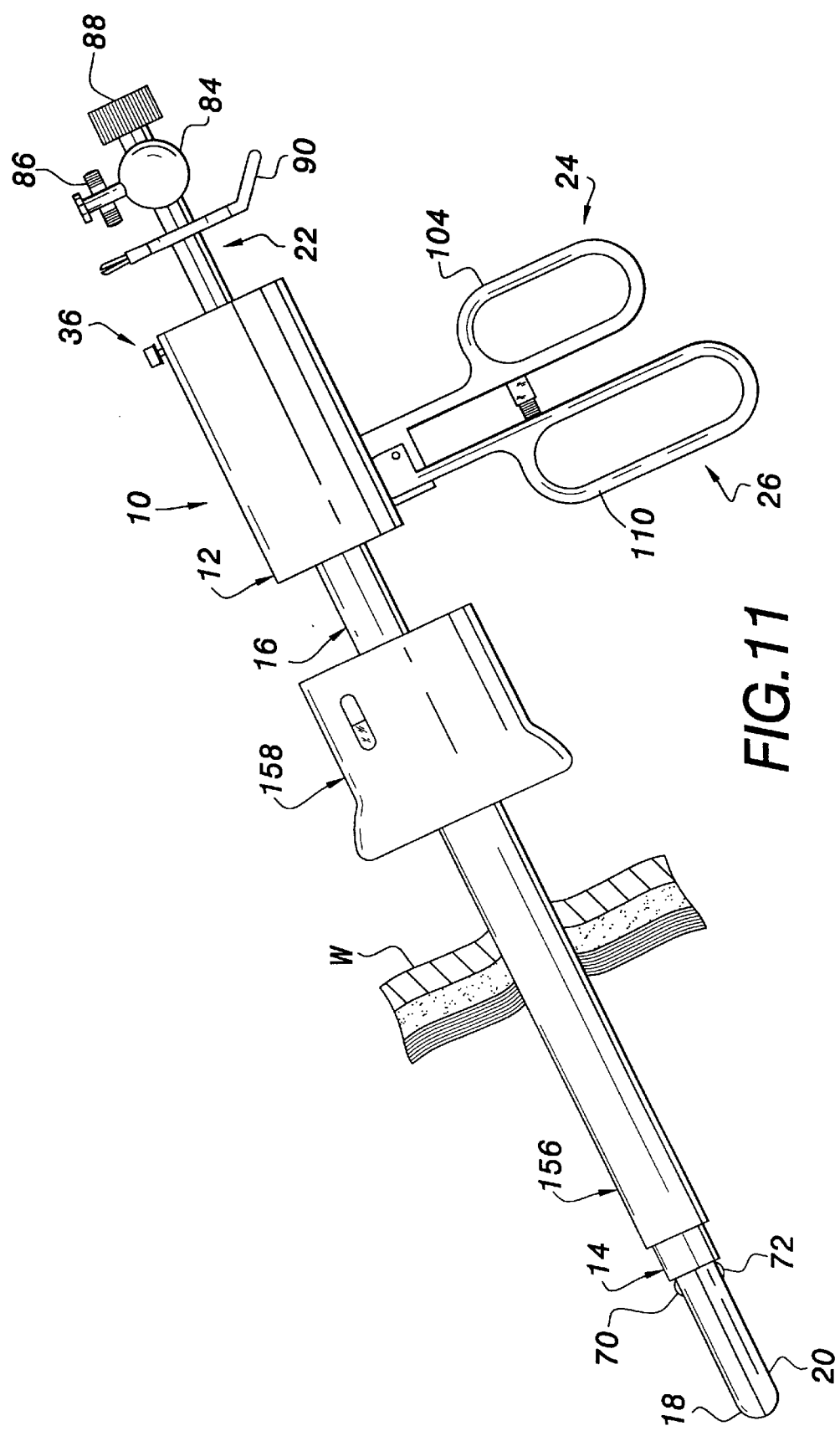
FIG. 11 illustrates the preferred embodiment in use.

With jaws 18 and 20 at least partly closed, endoscopic instrument 10 is inserted through portal sleeve 156 positioned within the anatomical cavity wall W, as shown in FIG. 11, to access an operative site within the anatomical cavity. Portal sleeve 156 can be positioned in the wall using any suitable penetrating technique, including those creating puncture sites by means of removable obturators such as trocars, and is shown carrying valve housing 158 at a proximal end to prevent the loss of pneumoperitoneum during insertion and withdrawal of endoscopic instrument 10. Visualization of the endoscopic procedure can be accomplished using a conventional endoscope (not shown) incorporated into endoscopic instrument 10, for example within tubular shaft 74, or separately positioned within the anatomical cavity through a second portal sleeve located at another puncture site.

Figure 12:
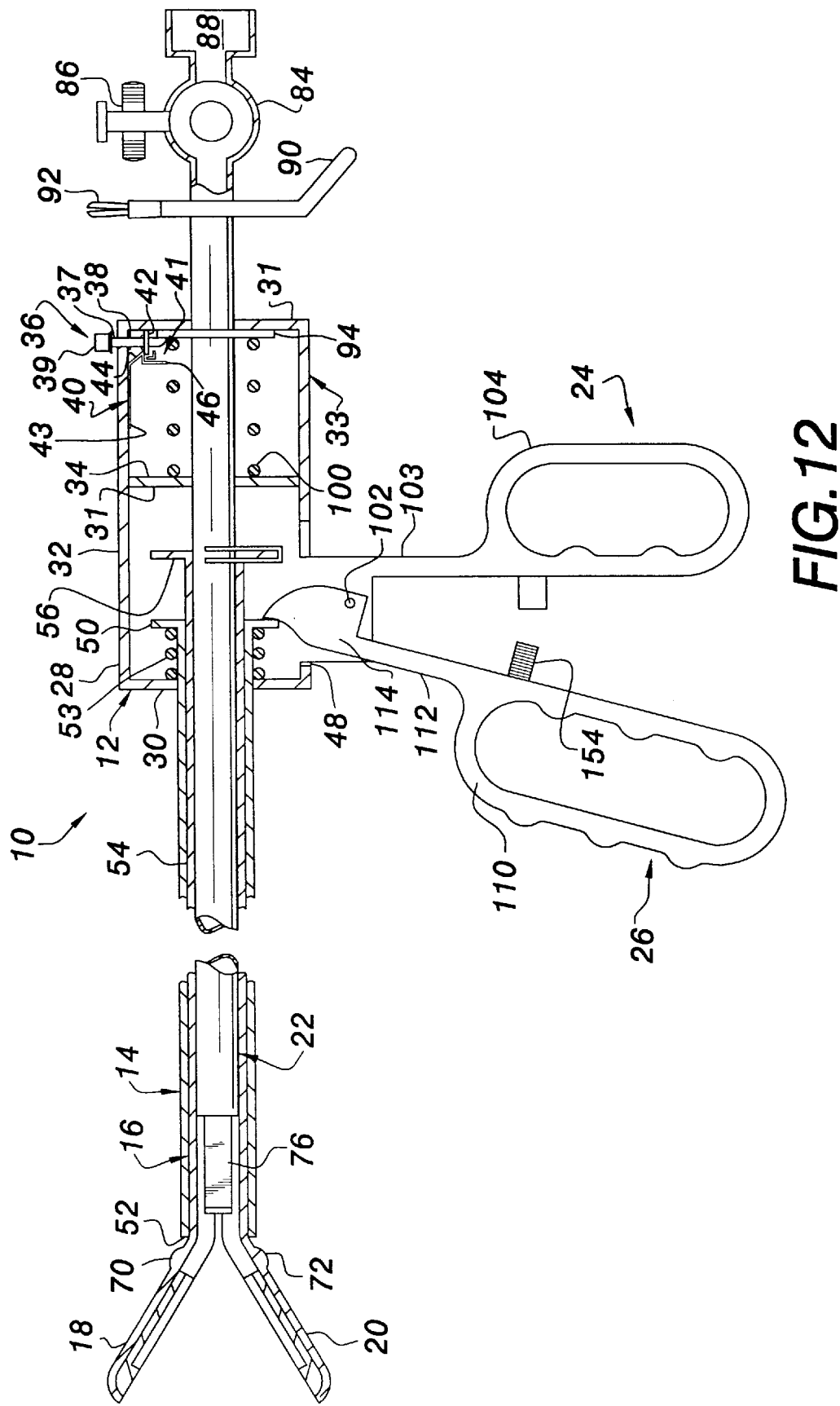
FIG. 12 is a sectional view of the preferred embodiment with the jaws open.
Figure 13:
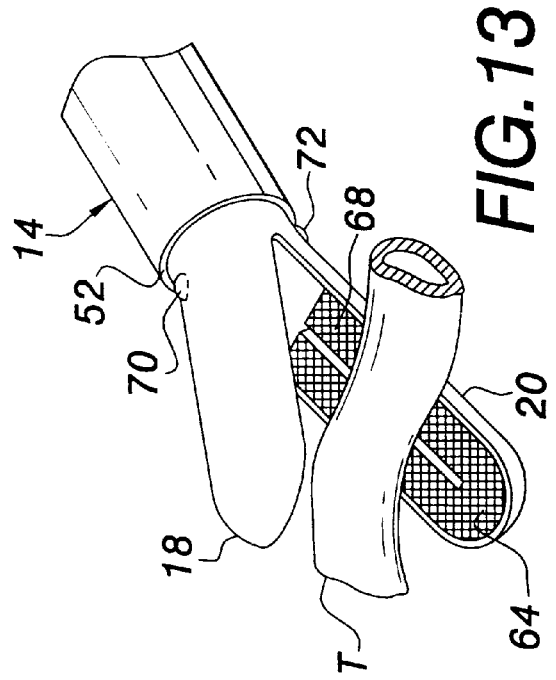
FIG. 13 illustrates the jaws of the preferred embodiment before grasping tissue.

Endoscopic instrument 10 is advanced distally through portal sleeve 156 until jaws 18 and 20 emerge into the anatomical cavity. At this point, jaws 18 and 20 can be opened to permit visualization by an endoscope through tubular shaft 74 or can remain closed in the case of using a separately positioned endoscope. If jaws 18 and 20 are to be opened, this is accomplished by exerting finger pressure on finger loops 104 and 110 to release protrusions 152 and 154 to spread finger loops 110 and 104 apart as shown in FIG. 12 due to the force of biasing member 53. Pivotal movement of finger loop 110 about pin 102 allows flange 50 to move proximally with respect to intermediate member 16 due to the force of biasing member 53. This causes distal end 52 of outer member 14 to slide off cams 52 and 72 in a proximal direction allowing jaws 18 and 20 to spread apart elastically, as illustrated in FIG. 12. Instrument 10 can be moved within the anatomical cavity with jaws 18 and 20 in either the open or closed condition depending on the type of visualization utilized and the desirability of presenting a narrow or wide jaw profile during movement. In FIG. 13, jaws 18 and 20 are shown in the opened condition for being positioned around anatomical tissue T to be grasped. Tissue T is located between tissue grasping inserts 62 and 64 so that when jaws 18 and 20 are partly closed, for example by placing finger pressure on the handles 24 and 26 to close jaws 18 and 20, tissue T will be held securely within the small gap between the jaws 18 and 20 as shown in FIG. 14.

Figure 14:
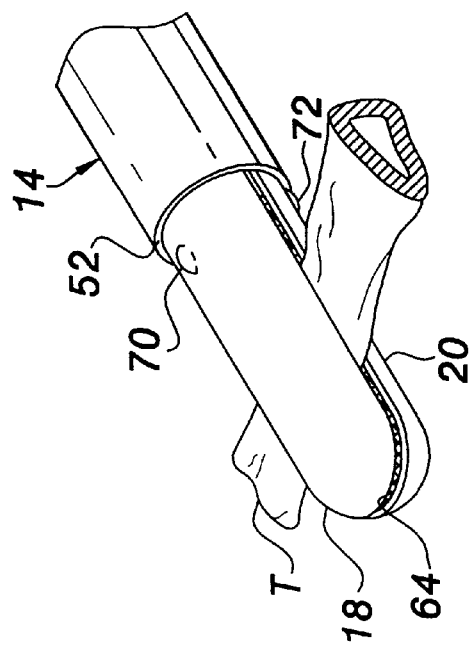
FIG. 14 illustrates the jaws of the preferred embodiment grasping tissue.

With tissue T firmly grasped between jaws 18 and 20, as illustrated in FIG. 14, inner member 22 can be advanced distally as shown in FIG. 15 to move blade 76 along insert grooves 68 thereby cutting through the anatomical tissue T held between the jaws. FIG. 15 shows, in phantom, an example of how the surgeon's hand can advance inner member 22. The tissue is not illustrated in FIG. 15 for clarity. First, safety mechanism 36 is released by pressing down on push-button 39 to cause annular flange 42 formed on post 37 to engage trigger leg 51 rotating the trigger clockwise in FIG. 2. Trigger 41 is spring-biased in a counterclockwise direction and will thus return to its original position once annular flange 42 advances beyond trigger leg 51. When pressure on the push-button 39 is released, safety bias member 38 will draw the post 37 upward in FIG. 2 so that the flange 42 will engage trigger leg 51 from the other side causing the trigger 41 to rotate counterclockwise and trigger leg 49 to bear against arm extension 46. Arm extension 46 and thus latching surface 45, are moved away from the post permitting bias member 38 to move the post to its unlocked position shown in FIG. 15 where the annular flange abuts the outer wall of the hub.

With safety 39 mechanism disabled, inner member 22 can be advanced by moving handle 90 toward housing 12 by pressure from the surgeon's thumb or other fingers. Blade 76 at the distal end of the inner member is aligned with the grooves 68 formed in jaw inserts 66, for example by use of splines formed along the length of the inner member, and is slidable along grooves 68 to cut any tissue held between jaws 18 and 20. Since grooves 68 in this embodiment do not extend the entire length of jaws 18, the distal ends of the grooves 68 can also serve as stops or abutments limiting the distal movement of blade 78 when jaws 18 and 20 are closed to protect surrounding organ structures. Tissue T can be cut completely or partly as desired and will be held between jaws 18 and 20 until the jaws are opened, allowing further procedures, such as cauterization, to be performed with tissue T immobilized. As mentioned previously, tubular shaft 74 is hollow and can thus be utilized for creating suction during the procedure, performing aspiration or irrigation or to facilitate passage of additional instruments or fluids into the anatomical cavity as desired. After a cutting procedure, blade 76 can be retracted from jaws 18 and 20 under the influence of bias member 100 or jaws 18 and 20 can be opened to release tissue T and instrument 10 can be withdrawn or used for another procedure.

Cutting can be accomplished without grasping using instrument 10 in the manner illustrated in FIG. 16. Use of the instrument 10 in this manner proceeds essentially as described above for a grasping and cutting procedure. However, inner member 22 is moved distally with jaws 18 and 20 in the open condition. With cutting edge 78 of blade 76 exposed, instrument 10 can then be advanced against anatomical tissue or other objects and suitably manipulated to create cuts of varying length and depth. Blade 76 can be locked in the extended position shown or any other position relative to housing 12 by use of additional safety mechanisms, like that of safety mechanism 36, or any other type of known locking mechanisms.

Figure 17:
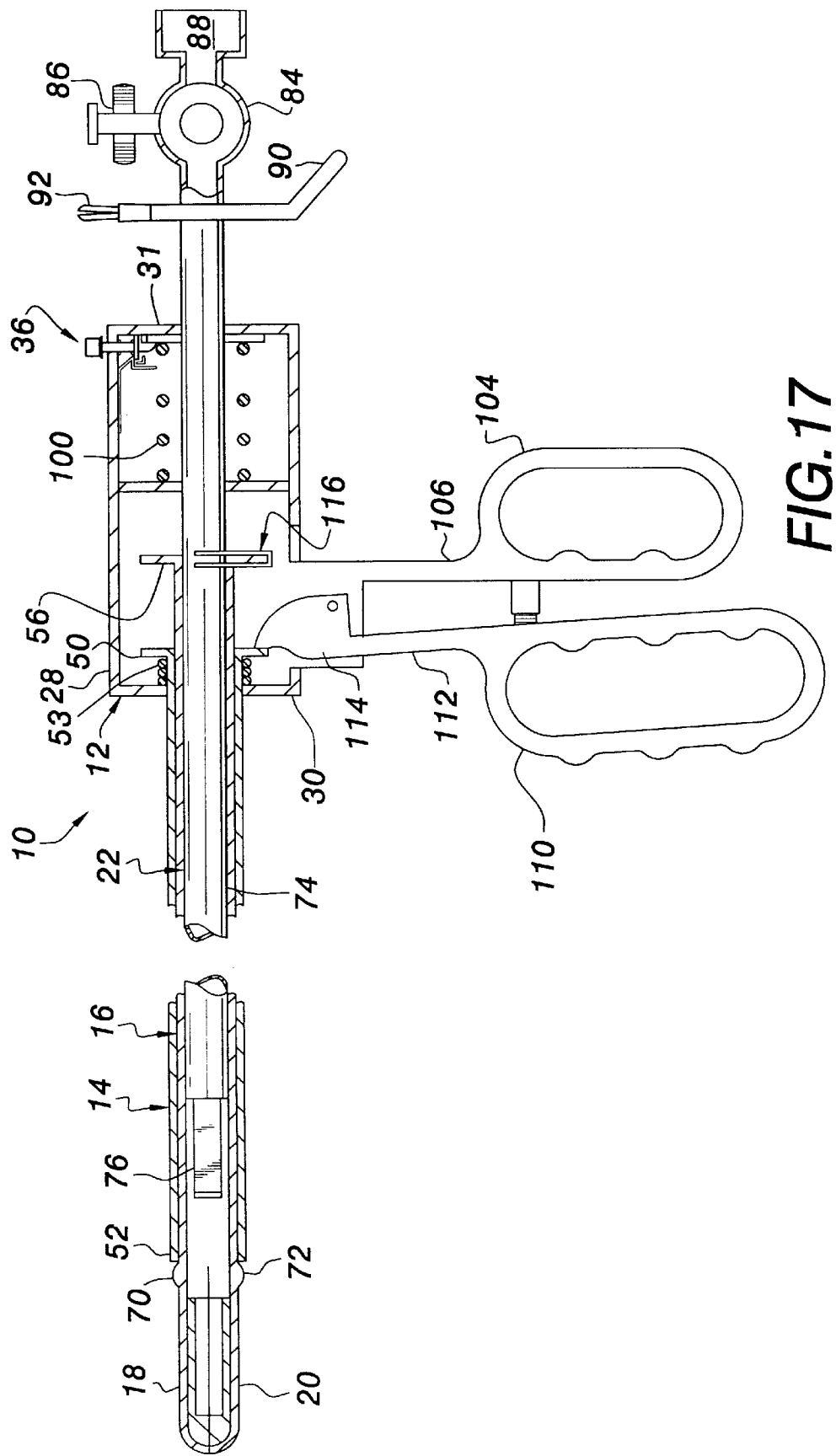
FIG. 17 is a sectional view of the preferred embodiment with the jaws closed and the inner member retracted.

As mentioned previously, tissue can be grasped and securely held with jaws 18 and 20 in a partly closed state. However, for certain procedures it may be desirable to draw jaws 18 and 20 completely together as shown in FIG. 17, with or without objects held between the jaws. Jaws 18 and 20 can be closed completely or clamped together by drawing finger loops 104 and 110 farther towards one another until distal end 52 of outer member 14 slides distally over cams 70 and 72 to an extent that forces jaws 18 and 20 into close contact with one another. If tissue or some other object is disposed between jaws 18 and 20, further advancement of outer member 14 over cams 70 and 72 will result in greater compression of the object. When loop handles 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied.

A modification of the endoscopic instrument 10 of the preferred embodiment is illustrated in FIGS. 18 and 19 wherein jaws 18 and 20 and tissue grasping jaw inserts 62 and 64 are formed as an integral one-piece unit and grooves 68 are made to extend along the entire length of the tissue grasping inserts 62 and 64 to define an aperture 158 at the distal end of jaws 18 and 20 when jaws 18 and 20 are closed. Aperture 158 can be used for extending blade 76 beyond jaws 18 and 20 even when closed (see FIG. 19) or for permitting passage of needles and other operating members through jaws 18 and 20 when closed. When blade 76 is permitted to extend beyond jaws 18 and 20, cutting can be accomplished without grasping as discussed above with respect to FIG. 16, with jaws 18 and 20 open or closed.

FIG. 20 shows a further modification of the endoscopic instrument 10 of the preferred embodiment in which jaws 18 and 20 include arcuate or concave portions 160 and 162, respectively, integrally-formed at opposed locations along the length of jaws 18 and 20. Arcuate portions 160 and 162 cooperate to define a substantially circular transverse passage through jaws 18 and 20 when closed and can thus hold a tubular organ, other anatomical tissue, or an object therebetween for being manipulated or cut, without compressing or flattening the organ, tissue or object. Tissue gripping surfaces 66 are formed on the flat portions of jaws 18 and 20 and can be formed along arcuate portions 160 and 162 as well. Grooves 68 are interrupted by arcuate portions 160 and 162 but extend longitudinally along flat portions of jaws 18 and 20 and are aligned to form a track for guiding blade 76 or other operating members across arcuate portions 160 and 162. When grooves 68 extend the entire length of jaws 18 and 20 as shown, grooves 68 can define an aperture such as aperture 158 at the distal end of jaws 18 and 20 to permit extension of blade 76 beyond jaws 18 and 20 shown in FIG. 19.

In yet another modification of the endoscopic instrument 10 of the preferred embodiment, shown in FIG. 21, lower jaw 20 is fixed and extends distally from tubular body 54 along a longitudinal axis of tubular body 54. Upper jaw 18 in FIG. 21 has cam 70 and is movable from an open position normally extending at an angle relative to the longitudinal axis of tubular body 54 to a closed position where it mates with fixed lower jaw 20. Fixed lower jaw 20 can also carry a cam 72. Jaws 18 and 20 include tissue gripping surfaces 66 and grooves 68 formed along the length thereof to serve as a guide for blade 76 and to form a distal aperture similar to aperture 158 shown in FIG. 19. Of course, this modification of the preferred embodiment can be operated in the same manner as described above.

FIG. 22 illustrates the distal end of a modified outer member 14. Slots 15 receive cams 70 and 72 to maintain alignment of jaws 18 and 20.

From the above, it will be appreciated that the endoscopic instrument of the present invention permits multiple functions to be performed endoscopically by use of a forceps unit having a tubular member with jaws configured for grasping or holding objects such as anatomical tissue or needles and an inner member having a shaft telescopically fitted within the forceps unit tubular member and carrying a blade. The tubular member and jaws of the forceps unit are preferably formed as an integral one-piece construction and are movably disposed within an outer tubular member to permit sliding movement of the outer tubular member over the jaws. The outer member and tubular forceps member can be mounted on a housing and coupled using any suitable handle mechanism and linkages for producing relative movement between the jaws and the outer tubular member. Because the jaws are carried at the end of a tubular body, the forceps unit can be positioned within an anatomical cavity with the blade of the inner member being advanced distally through the tubular body for performing different functions. The inner member can also be hollow and open at a distal end for facilitating visualization with a conventional endoscope, illumination with fiber optics or other suitable light sources, passage of implements such as ligature appliers to cooperate with instruments mounted at the distal end of the inner member tubular shaft, and/or for introducing or collecting fluids prior to, during or after an operative step is completed.

The jaws of the present invention can be straight, curved and/or angled and can have integrally formed or removable inserts with configurations for grasping and holding tissue and objects such as needles. Note that, while the jaws are discussed generally above as part of forceps, the jaws can be used to grasp a needle or any other object for suturing operations or the like. Thus the term "forceps" is used herein to describe any device for grasping tissue or other objects. The inserts can have any combination or number of longitudinal grooves for accommodating operating members such as blades, scissors, biopsy tools, needles, hooks, surgical clips or any other types of medical implements. The grooves can extend part way to define stops or abutments limiting distal movement of the blade or can extend the complete length of the inserts to form openings or apertures at a distal end of the jaws to allow passage of the blade beyond the distal end of the jaws when the jaws are closed. The jaws can have any shape in cross-section when closed, including circular, elliptical, rectangular and polygonal configurations, and can have opposed arcuate or concave portions for clamping tubular objects without compressing the objects.

Integral blades can be carried by one or both jaws and centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of the electrical connector disclosed herein is merely exemplary of the many various locations at which an electrical connector can be positioned. For example, an electrical connection could be made directly with the housing of the forceps to utilize the forceps jaws as conductive elements for performing electrosurgery. Also, inner surfaces of any of the tubular members, can be electrically insulated to permit passage of electrosurgical instruments therethrough.

The handles and linkages shown and described herein for sliding the outer member over the jaws are exemplary of the types of conventional handle mechanisms suitable for performing the function of closing the jaws. However, the handles can have any configuration for producing relative movement between the outer and intermediate members, including two pivoted legs with finger loops and sliding brackets as disclosed in parent application Ser. No. 08/376, 186, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired by selectively disengaging the handles from the jaws.

Suitable linkages include brackets with sliding motion, gears and/or racks mounted on or between handles and the outer and intermediate members, pulleys and cords or any other direct or indirect coupling mechanisms. The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for releasing or oppose the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost. The instrument can have various valves, stop cocks and seals to control fluid flow therethrough, such as the valve 150 schematically shown in phantom in FIG. 2.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
    a tubular outer member having a proximal end and a distal end;
    an intermediate member having a tubular body disposed telescopically within said outer member, a proximal end and a distal end defining a pair of opposed jaws;
    an inner member disposed at least partly within said intermediate member, said inner member comprising a shaft and a blade on a distal end of said shaft; and
    a handle coupled with at least one of said intermediate and said outer member and configured to move said pair of opposed jaws move between open and closed positions.

2. An instrument as recited in claim 1 wherein said jaws define opposed grasping surfaces.

3. An instrument as recited in claim 2 wherein a longitudinal groove is formed in one of said grasping surfaces.

4. An instrument as recited in claim 3 wherein said longitudinal groove extends part way along said one of said grasping surfaces to define a stop limiting distal movement of said blade advanced along said groove.

5. An instrument as recited in claim 3 wherein said longitudinal groove extends along an entire length of said one of said grasping surfaces to define an aperture at a distal end of said jaws.

6. An instrument as recited in claim 2 wherein a longitudinal groove is formed in each of said grasping surfaces.

7. An instrument as recited in claim 6 wherein said longitudinal grooves extend part way along said grasping surfaces to define a pair of stops limiting distal movement of said blade advanced along said grooves.

8. An instrument as recited in claim 6 wherein said longitudinal grooves extend along entire lengths of said grasping surfaces to define an aperture at a distal end of said jaws.

9. An instrument as recited in claim 1, further comprising:
    cam members disposed on outer surfaces of said jaws whereby said jaws are placed in the closed position when said distal end of said outer member is advanced distally over at least a portion of said cam members.

10. An instrument as recited in claim 1 wherein said jaws include opposed arcuate portions defining an opening between said jaws.

11. An instrument as recited in claim 1 wherein one of said jaws is fixed parallel to a longitudinal axis of said intermediate member and the other of said jaws is movable.

12. An instrument as recited in claim 1 wherein said shaft is tubular and has an open distal end and said blade is disposed diametrically across said open distal end of said shaft.

13. An instrument as recited in claim 12 wherein a longitudinal groove is formed in at least one of said jaws and said blade is arranged to slide along said groove when moved between said jaws.

14. An instrument as recited in claim 1 wherein said jaws are formed integrally with said distal end of said intermediate member.

15. A method of performing surgical procedures comprising the steps of
    introducing a tubular member having jaws through an opening in an anatomical cavity wall;
    grasping anatomical tissue with the jaws;
    advancing an inner member having a blade distally through the tubular member; and
    performing a medical procedure with the blade.

16. A method as recited in claim 15 wherein said introducing step includes closing the forceps jaws by sliding an outer member relative to the tubular member.

17. A method as recited in claim 16 wherein said grasping step includes sliding said outer member away from the jaws to permit the jaws to resiliently separate, positioning the anatomical tissue between the separated jaws and sliding the outer member toward the jaws to close said jaws around the anatomical tissue.

18. A method of performing surgical procedures comprising the steps of
    introducing a tubular member having jaws through an opening in an anatomical cavity wall;
    advancing an inner member comprising a blade distally through the tubular member until the blade protrudes distally from the jaws; and
    performing a medical procedure with the blade.

19. A method as recited in claim 18 wherein said introducing step includes closing the jaws by sliding an outer member relative to said tubular member to close the jaws and said advancing step includes moving the blade along a groove formed in at least one of the jaws.

20. A surgical instrument comprising
    a tubular outer member having a proximal end and a distal end;

an intermediate member having a body disposed at least partly within said outer member, a proximal end and a distal end defining a pair of opposed jaws;

an inner member disposed at least partly within a channel defined in said outer member, said inner member comprising a shaft and a blade on a distal end of said shaft; and a handle coupled with at least one of said jaws and configured to move said jaws between open and closed positions.

21. An instrument as recited in claim 20, wherein said channel passes through said intermediate member.

* * * * *